United States Patent [19]
Lane

[11] Patent Number: 5,964,736
[45] Date of Patent: Oct. 12, 1999

[54] LIVESTOCK BIOLOGICAL AND VACCINE HANDLING SYSTEM

[76] Inventor: Donovan R. Lane, P.O. Box 544, Paso Robles, Calif. 93447

[21] Appl. No.: 08/918,733

[22] Filed: Aug. 4, 1997

Related U.S. Application Data

[63] Continuation-in-part of application No. 08/532,055, Sep. 22, 1995, Pat. No. 5,733,258.

[51] Int. Cl.⁶ .................................................. A61M 5/315
[52] U.S. Cl. ........................... 604/220; 604/233; 604/207
[58] Field of Search .................................... 222/309, 439, 222/326, 157; 604/144, 232–234, 209, 211, 223, 224, 222, 136, 61, 220, 207

[56] References Cited

U.S. PATENT DOCUMENTS 3,905,365  9/1975  Colombo .
4,472,141  9/1984  Dragan .
4,968,303  11/1990  Clarke et al. .
5,733,258  3/1998  Lane .

*Primary Examiner*—Mark Bockelman
*Attorney, Agent, or Firm*—Dean P. Edmundson

[57] ABSTRACT

A closed delivery system is described for the handling of injectable biological products and vaccines used in the treatment and prevention of livestock diseases. This system embodies a multidose prefilled disposable cartridge and a metered pistolgrip syringe body. The cartridge is breech loaded into the syringe body and the product is dispensed from the cartridge by a unique drag link mechanism as a means for advancing the plunger rod and forcing the vaccine from the cartridge into the flesh of the animal being treated. Each prefilled cartridge is disposed of after it is emptied and no cleaning is required. A color coding system between the multidose, prefilled, disposable cartridges and the syringe bodies insure that proper dosages are given and that products are not mixed up or confused by the technicians administering the products.

11 Claims, 5 Drawing Sheets

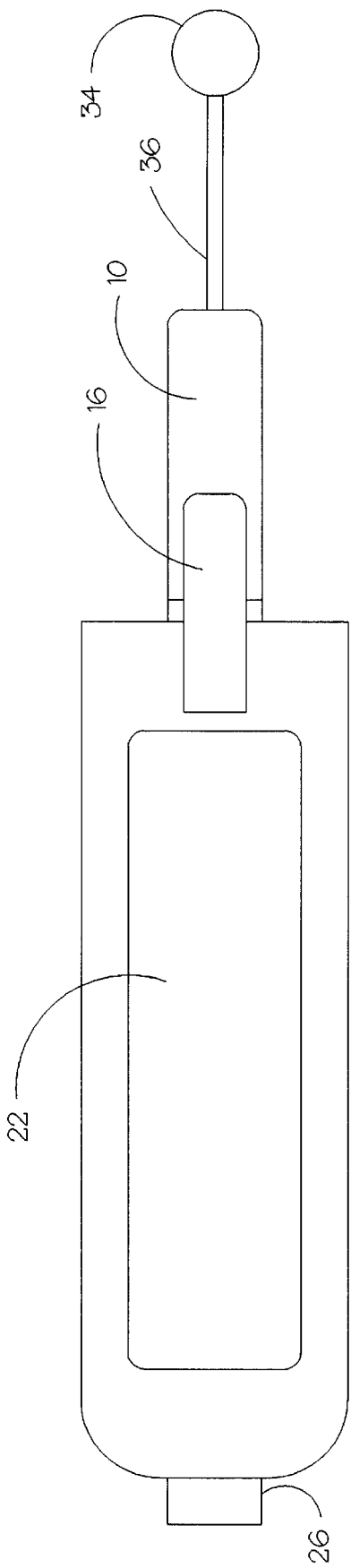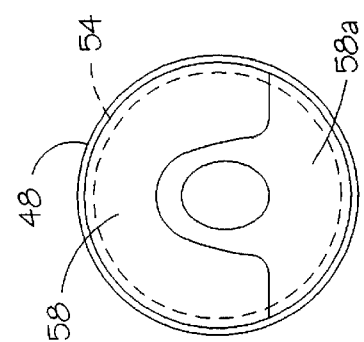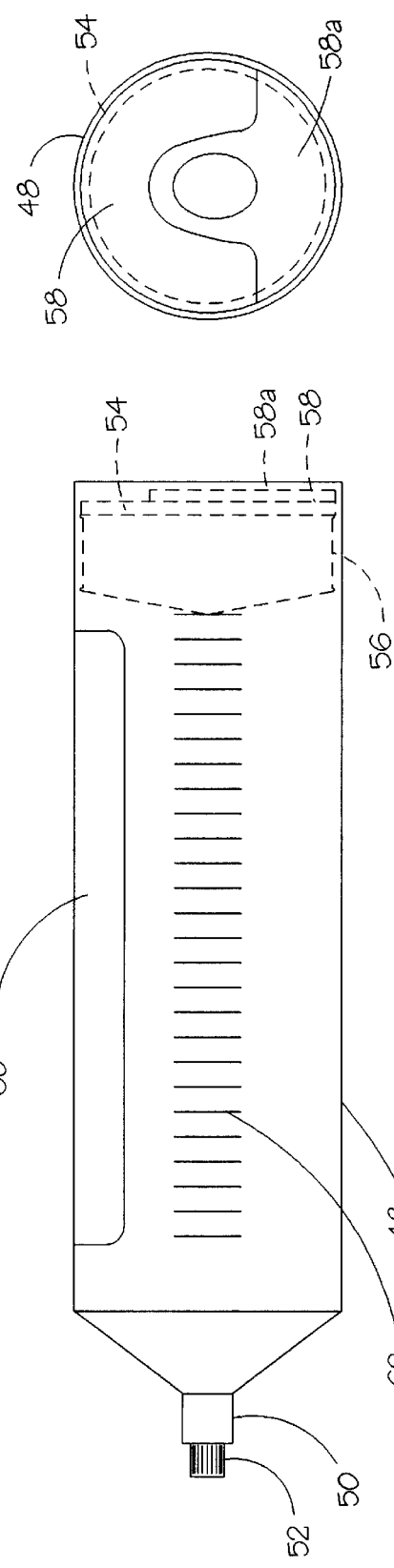

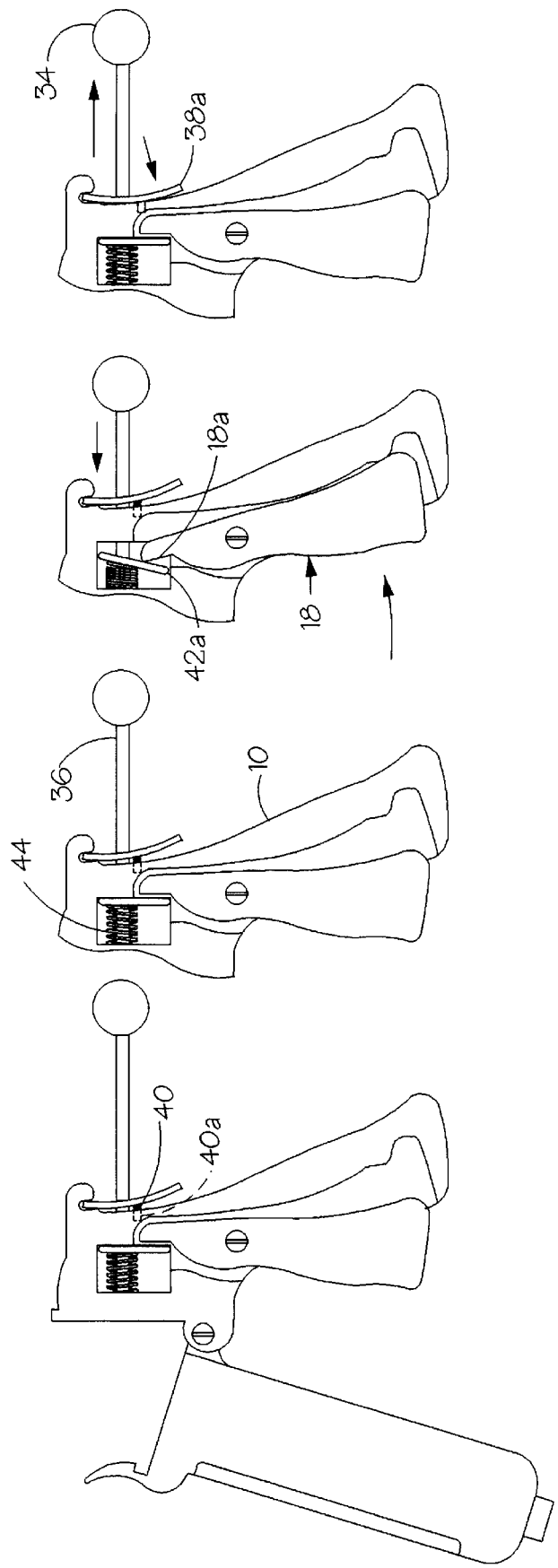

LIVESTOCK BIOLOGICAL AND VACCINE HANDLING SYSTEM

CROSS REFERENCE TO RELATED APPLICATION

This application is a continuation-in-part of my application, Ser. No. 08/532/055, filed Sep. 22, 1995 now U.S. Pat. No. 5,733,258.

BACKGROUND-FIELD OF INVENTION

This invention relates to multidose, medical injection syringes used for the vaccination and treatment of livestock diseases. More specifically, it relates to a process and a closed handling and delivery system for those injectable animal health products used in syringes to include all the steps from the packaging of the product at the pharmaceutical company to the actual injecting of the livestock on the farm.

BACKGROUND-DESCRIPTION OF PRIOR ART

Heretofore, multidose, metered, pistol grip type livestock syringes have generally been made from a combination of casted and machined metal parts with glass or plastic barrels sealed on each end with rubber washers. Usually a rubber like plunger is used to force the product from the barrel, through the needle and into the flesh of the animal being injected. This process involves the transferring of the biological product from the package container into the barrel of the syringe allowing for contamination of the product in a multitude of ways. Other numerous disadvantages to these conventional types of livestock syringes and the standard process for the handling of these biologicals are listed below.

(a) The biologicals are packaged at the pharmaceutical companies in glass or plastic containers sealed with a rubber stopper seal, generally in quantities of ten to one hundred doses. At the farm, the technician will transfer the biological from the container to the syringe. Sterile medical procedures and expensive sterilization equipment are not common to most farm operations. Consequently the biologicals are easily contaminated by outside air and non-sterile syringe parts such as the needles used to pierce the rubber seal of the vaccine container, the contaminated syringe barrel, the seals at each end and the plunger of the syringe. Contamination also occurs during the refilling of the syringe as a contaminated needle is pierced through the rubber seal of the standard vaccine bottle and a charge of contaminated air is forced into the bottle to provide back pressure to refill the syringe. The technician may reenter the vaccine bottle five to ten times for refilling before the bottle is empty. In addition it is not uncommon to vaccinate 100 or more head of cattle with the same needle before switching to a clean needle. The more times the vaccine bottle is reentered and the longer the same needle is used, the greater the contamination to the product and the animals being vaccinated. The greater the contamination, the greater the number of cysts and lesions will be found on the carcasses after slaughter. In addition cross contamination causes the rapid spread of many diseases within the herd.

(b) Slow refilling is another problem. The standard syringe in use today will only give ten or twelve 5 cc doses before it is ready to be refilled. Drawing the high viscosity vaccine into the syringe makes refilling very slow at the working chute.

(c) There are many adjustments on these standard type syringes and many places for them to leak, a constant source of complaints from the technicians. All the rubber gaskets and washers must be in excellent condition and the plunger tension adjusted perfectly to avoid any leakage and even breakage of the syringe barrel.

(d) Most of these pistol grip syringes have a pawl and ratchet type mechanism for advancing the plunger and metering the dosage. If the dosage meter is accidentally set wrong or bumped out of adjustment, a wrong dose will be administered and the mistake may not be detected until after several, maybe many, animals have been given the wrong dose. Also as the teeth on these ratchets wear down and the springs become weaker they will occasionally skip a notch thereby administering a "short dose". It is difficult to detect the difference between a four milliliter dose and a five milliliter dose, based on the feel of the trigger so the technician may be unaware that he has been giving short doses.

(e) In general, these metal and glass syringes are relatively expensive. They have a multitude of replaceable parts which are not interchangeable between the different brands of syringes. It therefore becomes difficult to find a farm supply store with an adequate inventory of parts for all guns.

(f) If the metal syringe is equipped with a glass barrel, it can easily be broken causing the loss of expensive product and time. If it is equipped with a plastic barrel it may become out of round and begin to leak.

(g) When several different vaccines and biological products are being used, mix ups often occur. The mix ups usually occur during the refilling process when several technicians are working in the same area giving a series of injections to animals as they come through the working chute. The syringes all look the same and many of the biological products are similar in color and consistency. Consequently it is not uncommon for the wrong product to be loaded into the wrong syringe.

Prefilled cartridges heretofore, have generally been utilized in single dose human applications and occasionally have been tried for livestock, again mostly as single dose ampoules or cartridges. The ampoule may have a pierceable membrane, to be perforated by a needle that is sharpened on both ends and fixed to the syringe body, not the cartridge. This was the method used in the U.S. Pat. No. 2,778,359 to Freidman (1957) and several other syringes that have followed, mainly designed for human use. Multidose, metered, pistolgrip syringes became popular for livestock use during the 1960's and the basic state of the art is best characterized in the U.S. Pat. No. 3,110,310 to Cislak (1961). To fill this syringe the needle of the syringe is pierced through the rubber seal of the vaccine bottle and a charge of air is pushed into the bottle to supply the needed back pressure. The vaccine or biological product is then drawn from the original package or bottle into the syringe by pulling rearward on the plunger rod. The biological is dispensed when the trigger is squeezed and a pawl attached to the trigger mechanism pushes against a notch on the plunger rod to advance the plunger rod. Generally each notch on the plunger rod represents one milliliter of biological product dispensed and the syringes are adjustable between one and five milliliters. These type syringes are not specific to any one product and with the adjustment feature, allow for both human and mechanical errors in dosage size. Relatively few significant improvements or modifications have been made in this standard type of pistol grip syringe over the past 35 years.

A marriage between a metered, multidose, pistol grip syringe and a prefilled cartridge was attempted in U.S. Pat.

No. 3,517,668 to Brickson (1970). A pierceable cartridge and a needle sharpened on both ends was used, preventing the system from being classified as a completely closed system, since the needle is fixed to the syringe and could likely be used to pierce more than one cartridge, therefore contaminating all the cartridges following the first one used. In addition a half used cartridge cannot be stored and later reused and maintain its closed system status because the seal has been pierced and the cartridge is not married to the needle with which it was first used. The mechanism of the trigger and plunger rod advance system are somewhat complicated and are not skip proof because the springs will weaken and the pawls and ratchet notches will wear down with use. This appears to be a rather slow loading syringe because the barrel must be unscrewed, the cartridge loaded into the barrel and the barrel screwed back onto the syringe body. U.S. Pat. No. 4,368,731 to Schramm (1983) utilizes a glass ampoule with a permanently affixed needle. If that needle is bent or broken the ampoule is no longer usable. This syringe also requires unscrewing and screwing the barrel to load the ampoule. A devise for oral application of gels and pastes is described by Young et al. in his U.S. Pat. No. 4,425,121 (1984). This applicator employs a screw on tube or cartridge and a ratchet and pawl mechanism for advancing the plunger. U.S. Pat. No. 4,472,141 to Dragan (1984) is a pistol grip syringe designed for dental applications and utilizes a variety of frontal screw on mounted tips and cartridges for various dental applications. The plunger rod is advanced through the use of a complicated ratchet and pawl mechanism.

The syringe with the closest relationship to my invention is U.S. Pat. No. 4,738,664 to Prindle (1988). This syringe is similar to the Cislak syringe but has been adapted to hold a modified disposable syringe which is bayonet mounted onto the front of the original pistol grip mechanism. The use of a prefilled cartridge is not indicated for this syringe. The vaccine must still be drawn from the bottle into the syringe. The advantage over the original Cislak syringe is that no cleaning is necessary. The syringe barrel is disposed of after the vaccinations are completed. This syringe, however, is not a closed system because the product must be transferred from the package or bottle into the syringe. In addition the mounting of the disposable syringe is somewhat cumbersome in that the disposable syringe must first be twist lock connected to the pistol grip mechanism and then the plunger rod is twist lock coupled to the plunger. Finally, a support is wedged onto the end of the disposable syringe but no real support is provided for the full length of the apparatus. U.S. Pat. No. 4,968,303 to Clarke et al (1990) is a pistol grip syringe specifically designed to handle single dose cartridges for a specific product. One injection is made and the cartridge is discarded and a new one loaded for the next animal to be injected. There is no plunger brake and when the squeeze pressure on the trigger and handle is released the plunger rod is retracted to its' original position. The needle is permanently fixed to the cartridge as in the Schramm syringe, so that it is not replaceable if bent or broken.

OBJECTS AND ADVANTAGES OF THE PRESENT PATENT

This invention combines a unique cartridge package for vaccines and other injectable biologicals with an innovative new pistol grip syringe body to form an entirely new closed delivery system concept or process for the handling of injectables for use in livestock. At the pharmaceutical company the animal health product will be packaged in sterile cartridges. The cartridge will be sealed on the anterior or needle end. The posterior end of this cylindrical cartridge will be primarily sealed by the insertion of a rubber or rubber-like plunger. In addition a color coded seal will seal the posterior end of the cartridge. The cartridge will be labeled with a colored label which will in turn indicate the color of the syringe body with which it is to be used. At the farm supply store the customer will be sold or given the proper colored syringe body to match the color of the cartridge label of the biological product that the customer has purchased. That specific colored syringe body has been pre-metered to dispense only the precise dosage recommended for the product with the matching colored label. If the label on the cartridge is green, it shall only be used with a green syringe body, for example. If the required dosage for the green packaged product is 5 milliliters, the green syringe bodies will be metered to dispense precisely 5 milliliters per full squeeze of the trigger. There will be no adjustments for dosage level on these syringe bodies thererby eliminating the possibility of human error. The dosage level for another product may be 2 milliliters and the cartridge may have a yellow label. The syringe body distributed with that product will be yellow and will dispense only 2 milliliters of product per squeeze. The dimensions of the cartridge itself and the dimensions of the barrel of the syringe body will be such that a cartridge requiring one specific dosage level will not fit into or function in a syringe body that is engineered to administer a different dosage level. The technician at the farm will tear away the posterior seal and load the cartridge into the syringe, just as shells are loaded into a breech loading shotgun. The twist off cap seal will be removed from the needle adapter on the cartridge, a sterile needle is twist locked onto the needle adapter and the vaccinating will begin. Thus, the biological product has remained completely within a closed system from the time it was sealed under sterile conditions at the drug manufacturer until the cap seal was removed from the cartridge on the farm.

(a) The combination of this entire process and the mechanical aspects of the designed cartridges and syringe bodies will insure that the original sterile condition of the product will be maintained from the manufacturer until the product is injected into the livestock. All chance of contamination, either mechanical or airborne, as was described in part (a) under BACKGROUND and PRIOR ART (above), has been eliminated because the product has been contained within this closed delivery system from packaging until injection. This cleaner, more sterile process of injecting livestock will produce an immediate drop in injection site lesions and cysts and a reduction in diseases and illnesses transmitted from animal to animal through the use of contaminated instruments.

(b) Reloading will be rapid and simple. When the cartridge has been spent, the syringe body will be opened, just as a breech loaded shotgun is broken open. The spent cartridge and attached needle are discarded into the trash and a new prefilled cartridge is loaded into the syringe body. The syringe body is then snapped closed, the cap seal is removed, a sterile needle is attached and the syringe is again ready for use. A unique closure latch secures the syringe barrel in the closed position.

(c) There will be no leakage with this syringe body because all the mechanical and adjustable parts that come in direct contact with the biological product, and are usually the source of leaks in the current state of the art syringes, have been eliminated and replaced by disposable cartridges with their own plungers which, of course, are new with each cartridge change.

(d) The mechanism that forces the plunger rod forward in this invention is a free floating drag link and has absolutely no adjustment. As the center pivot trigger is squeezed ,the top of the trigger pushes on the bottom of the free floating drag link, which in turn, binds on the plunger rod, advancing or dragging it forward. This combination of leverage and binding action will not allow any skips or improper sized doses to be given. Currently used ratchet and pawl mechanisms rely upon a small delicate spring to hold the pawl in the notch. In addition the inevitable wearing and rounding off of the tiny teeth on the pawl and the plunger rod in these type mechanisms ultimately cause skipping and the administering of improper sized doses. The standard syringes being used today, after some wear and tear, may skip a notch and only give 4 milliliters instead of 5 and that slight difference in dosage cannot easily be detected by the technician as he is operating the syringe.

(e) These closed delivery system syringe bodies of the present invention are preferably made from hard plastics through the injection molding process and will be relatively inexpensive compared to the machined metal syringes on the market today. As is shown in the accompanying drawings, they are a very simple mechanism and consequently very light weight and easy to handle. Because of the low cost, drug manufacturers may elect to give the syringes to the buyers of larger quantities of the animal health products. These syringes will be made from durable hard plastic and hardened metal parts, so their wear life will be comparable to the all metal syringes. However if they should break or fail in some way, they will be inexpensive enough to replace rather than repair.

(f) With no glass in the construction of this syringe, the problems of product loss and work slowdowns to replace the broken glass barrels are eliminated.

(g) Mixing up or confusing the vaccines in the working area is a very common problem and the wrong vaccines are often, inadvertently refilled into the wrong syringes. This happens because the color and consistency of many of the vaccines are very similar and are often packaged in similar appearing containers. With this unique color coded system of the present invention, the technician is not even required to be able to read the label to get the proper product into his syringe and administer the proper sized dose. All he or she must know is that the yellow cartridges go in the yellow syringe body, the blue cartridges in the blue syringe body and so on. The technician won't even need to adjust the dosage level or the tension on the plunger. He can't because there are no adjustments. In addition, the technician cannot inadvertently load a 2 milliliter dose size cartridge into a syringe body engineered to administer 5 milliliter doses, because it will not fit. The dimensions of the cartridge and the dimensions of a differently colored syringe body barrel will be different.

(h) Each syringe body is precalibrated to give only one dosage level with one full trigger travel (i.e. one squeeze of the trigger) and is color coded for a specific product with this predetermined dosage level, therefore eliminating any need for adjustments to the syringe.

(i) With all of the above mentioned advantages to this system, the one most popular with the farmers and ranchers will be that no cleaning of the syringes is necessary, yet absolutely sterile conditions will be maintained. Also correct dosages of each different type of vaccine are assured.

Further objects and advantages of this new process and accompanying syringe body and cartridges will become apparent from consideration of the ensuing drawings and description.

BRIEF DESCRIPTION OF THE DRAWINGS

FIG. 2 is the top view of the same syringe body.

FIG. 3 is the side view of the sealed, multidose, prefilled cartridge.

FIG. 4 is the rear view of the same cartridge.

FIG. 5 shows the barrel position pivoted to an open position to facilitate breech loading.

FIG. 6a shows the trigger in the resting position.

FIG. 6b shows the trigger in the squeezed position.

FIG. 6c shows the plunger rod brake in the released position.

Figure 1:
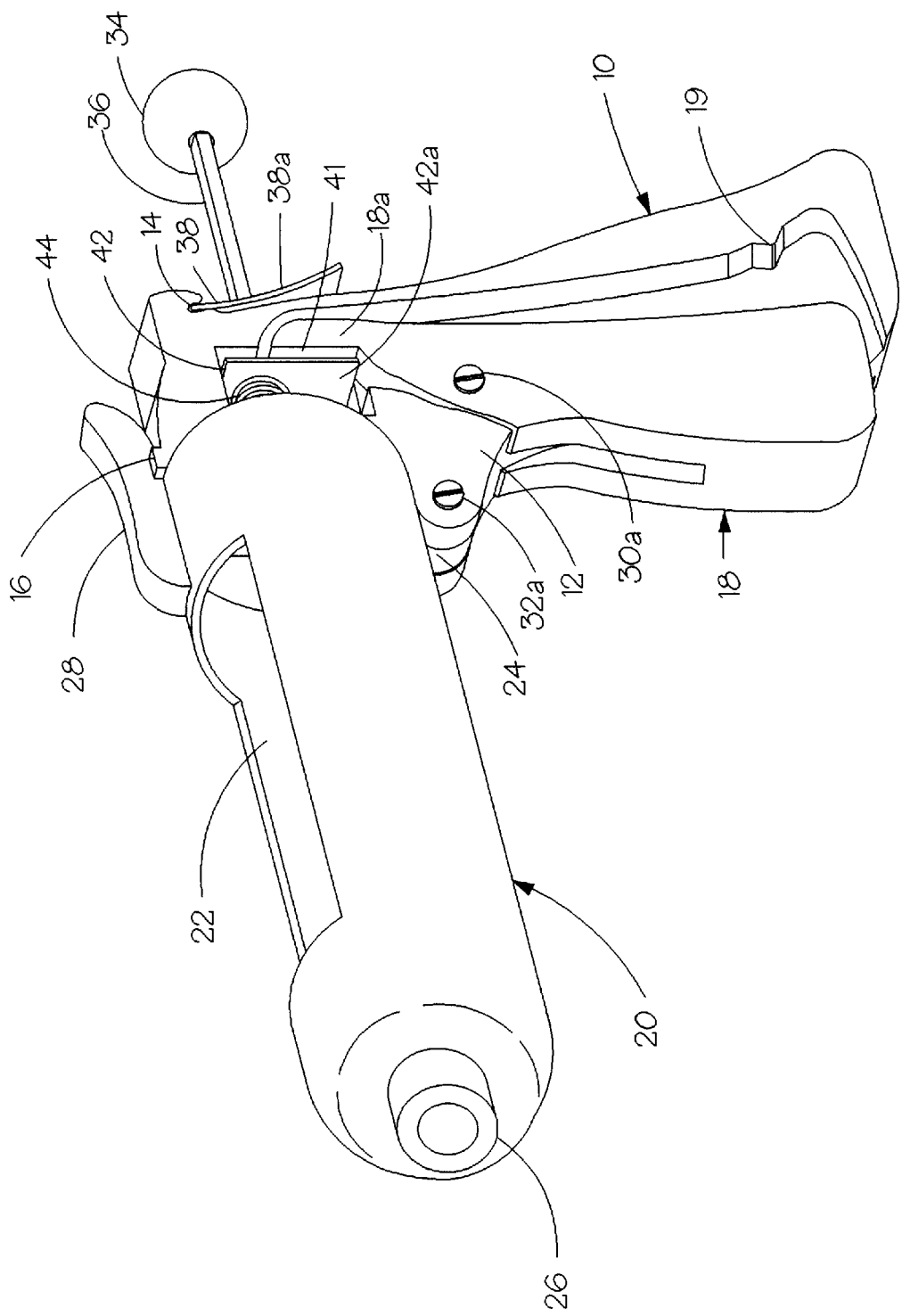
FIG. 1 is the side view of the pistol grip syringe body with no cartridge loaded.

| Reference Numerals in Drawings | |
|---|---|
| 10 main body frame | 38 plunger rod brake |
| 11a main body frame aperture | 38a lower end of plunger rod brake |
| 11b main body frame aperture | 38b plunger rod brake aperture |
| 12 loading pivot base | 40 brake tension spring |
| 14 plunger rod brake pivot | 40a spring support hole |
| 16 closure latch receiver | 41 operation window |
| 18 center pivot trigger | 42 drag link |
| 18a striking surface of the trigger | 42a lower end of drag link |
| 19 trigger stop | 42b drag link aperture |
| 20 barrel | 44 main spring |
| 22 observation window | 46 plunger pusher |
| 24 loading pivot at rear of barrel | 48 multidose disposable cartridge |
| 26 needle protector collar | 50 twist lock needle adapter |
| 28 closure latch | 52 twist off cap seal |
| 30a trigger pivot sleeve screw | 54 plunger retention ring |
| 30b threaded sleeve | 56 plunger |
| 32a loading pivot sleeve screw | 58 color coded posterior seal |
| 32b threaded sleeve | 58a pull ring |
| 34 plunger rod handle | 60 color coded label |
| 36 plunger rod | 62 dosage increment marks |

DETAILED DESCRIPTION OF THE INVENTION

The essence of this invention combines the mechanical aspects of the items in FIGS. 1 through 8 to create a product or system referred to herein as a closed delivery system for the administration of injectable vaccines and biological products used in the treatment and prevention of diseases and ailments in livestock. The goals of this system are as follows:

(a) Create maximum sterile conditions and eliminate any chance of outside elements contaminating the biological product. This is done through a closed delivery system where the product is packaged and sealed under absolutely sterile conditions at the pharmaceutical manufacturer and remains sealed until the animal is actually injected with the product.

(b) Create a system that is economically competitive with the current state of the art practices and is faster and simpler to use than these methods we are using today.

(c) Create a system or process where the technicians on the livestock processing crews can load and reload their syringes rapidly without the chance of mixing up the products or the syringes, especially between the workers on the crew.

(d) Create a system where no cleaning or sterilization of injection instruments is required.

(e) Create a system that insures proper dosages are given and eliminates the chance for human or mechanical error in dosage levels by eliminating adjustments.

This process or closed delivery system, encompasses three basic elements to accomplish the goals listed above.

Figure 8:
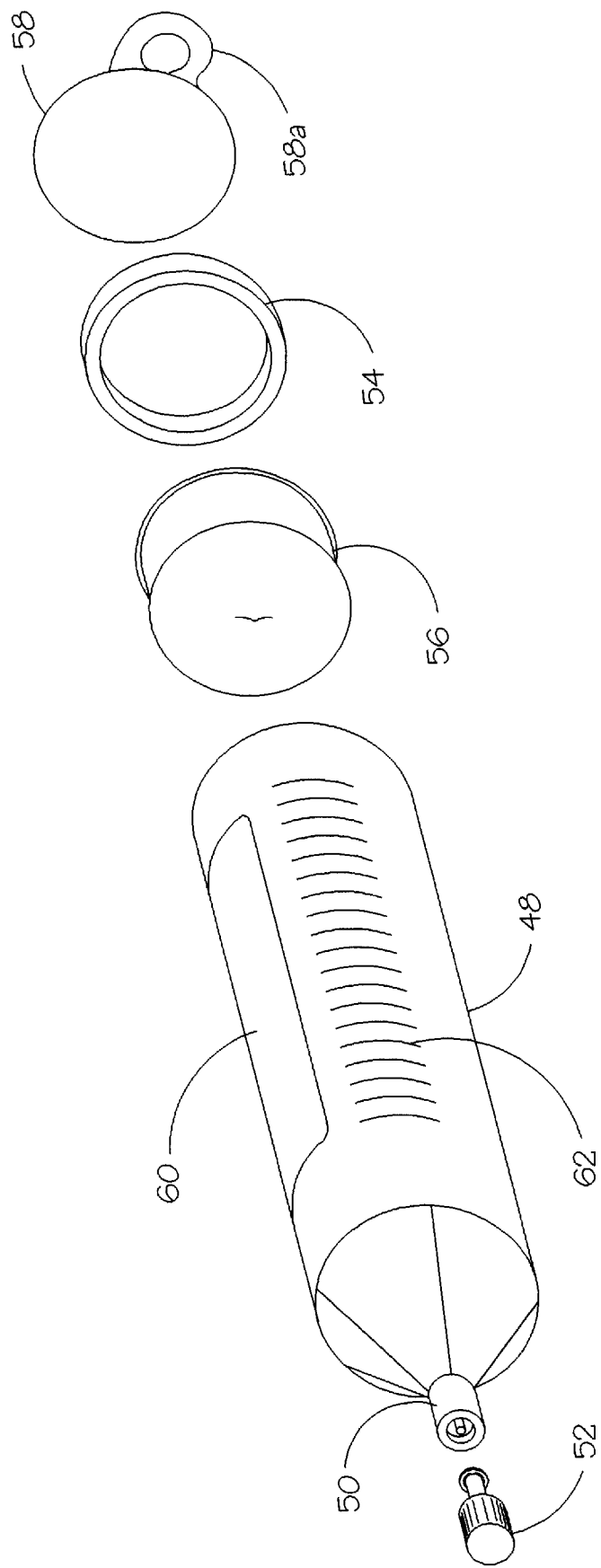
FIG. 8 is a ¾ exploded view of the cartridge.

(1) The packaging of the product in sealed, sterile, disposable, multidose cartridges 48, as is illustrated in FIGS. 3, 4 and 8.

(2) The color coding system between the cartridges and the syringe bodies or dispensing members.

(3) The light weight, quick loading and inexpensive syringe body illustrated in FIGS. 1, 2, 5, 6a, 6b, 6c and 7, designed to accommodate the above cartridges 48.

Figure 7:
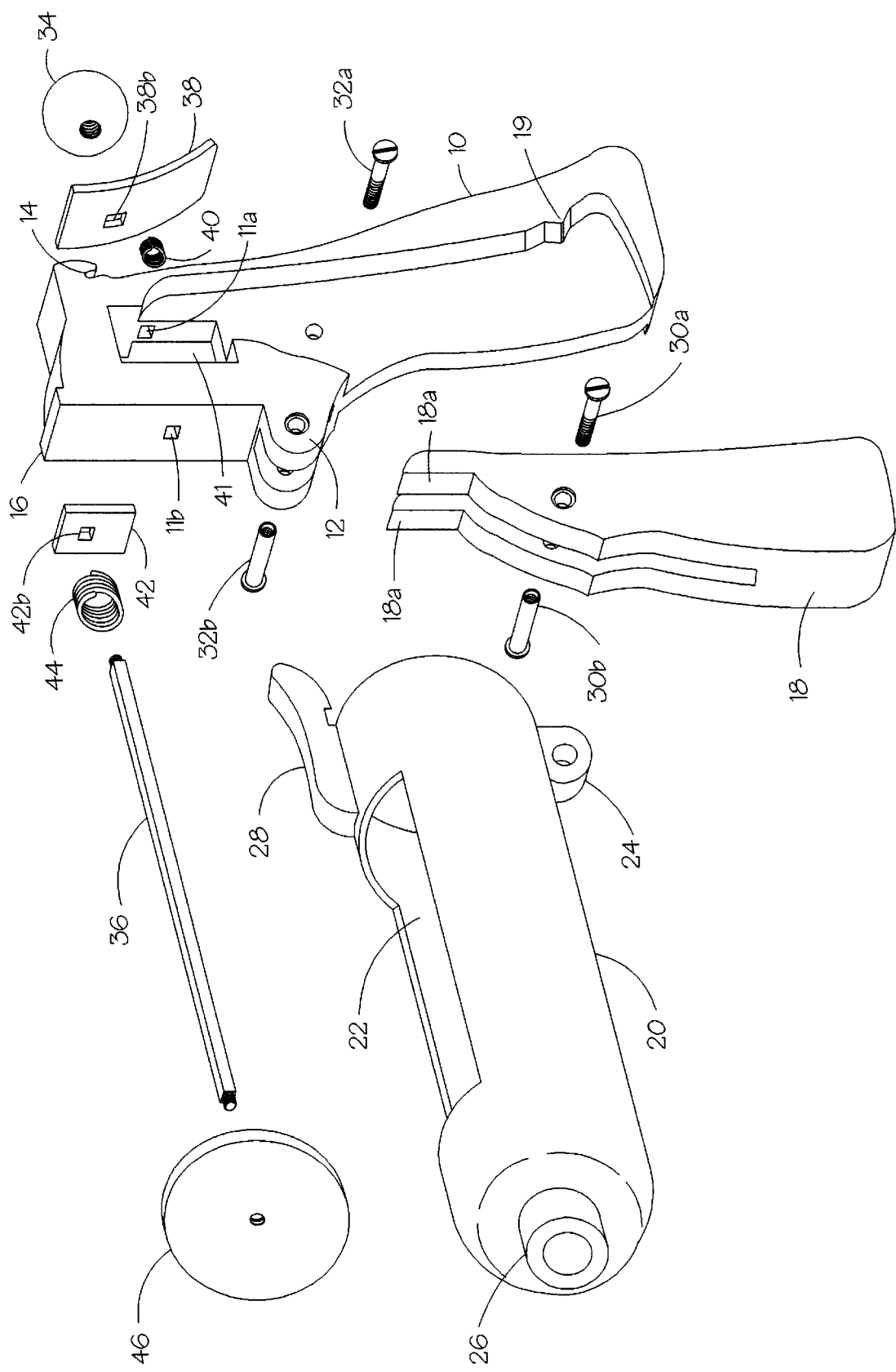
FIG. 7 is a ¾ exploded view of the syringe.

A preferred embodiment of the syringe is illustrated in FIGS. 1, 2, 5, 6a, 6b, 6c and 7 and detail of the disposable cartridge is illustrated in FIGS. 3, 4 and 8. These are the two basic mechanical elements of the invention that combine to form a process or closed delivery system designed to simplify and cheapen the vaccinating process and improve the sterile nature of injectable animal health products used in the prevention and treatment of livestock diseases. The cartridge 48, as shown in FIGS. 3, 4 and 8, is a cylindrical, hollow tube made of an unbreakable, transparent, plastic like substance. The anterior end of the cartridge 48 is necked down to a twist lock needle adapter 50, sized to accommodate a standard disposable injection needle. The needle adapter 50 is sealed with a twist off cap seal 52. The injectable product is sealed in the cartridge 48 on the posterior end by the insertion of a plunger 56. A plunger retention ring 54 is inserted into the posterior end of the cartridge 48 to prevent any internal pressure within the cartridge 48 from forcing the plunger 56 out of the cartridge 48. Each loaded cartridge 48 is labeled with a specific color coded label 60 and secondarily sealed on the posterior end with a color coded posterior seal 58 also colored to match the label 60. A pull ring 58a is shown to facilitate the removal of the color coded posterior seal 58. Each separate injectable product cartridge will have its own unique color, which will be used for the color coded label 60, the color coded posterior seal 58 and the syringe body, also color coded, shown in FIGS. 1, 2, 5, 6a, 6b, 6c and 7. The dimensions of the cartridge 48 and the syringe barrel 20 will be such that cartridges 48 will only fit and function in the barrels 20 of syringe bodies engineered to dispense the precise dose recommended by for the product contained in that cartridge 48. The cartridge 48 is marked with dosage increments 62, which can be viewed through the observation window 22 of the syringe body as shown in FIGS. 1, 2 and 7, to give the technician an indication of how many doses have been used and how many doses remain in the cartridge 48.

The exploded view of FIG. 7 shows detail of the parts of the pistol grip syringe body or dispensing member. The barrel 20 is cylindrical in shape with an inside diameter of the proper dimension so that the cartridge 48 will slide into the barrel 20 with a fairly snug fit. On the anterior end of the barrel 20 is a thickened needle protector collar 26 with an inside diameter of sufficient size to allow a snug fit for the twist lock needle adapter 50 of the cartridge 48 when the cartridge 48 is breech loaded into the barrel 20. FIG. 5 shows the syringe body with the barrel 20 pivoted to the open position to accommodate the breech loading of the cartridge 48 into the barrel 20 of the syringe body. An observation window 22 in the top of the barrel 20 allows a means for the technician to observe the movement of the plunger 56 as it advances through the cartridge 48. The closure latch 28 is molded onto the top, posterior end of the barrel 20. The loading pivot 24 is molded to the posterior bottom end of the barrel 20 and it includes a hole or aperture as a means for fastening the barrel 20 to the main body frame 10 at the loading pivot base 12. The main body frame 10 is the sturdy central structure of the syringe body to which most other parts of the syringe body are attached or operated from. The mounting of the loading pivot 24 to the loading pivot base 12, fastened with the loading pivot sleeve screw 32a and threaded sleeve 32b allows the barrel 20 to pivot axially from the main frame 10 as a means for breech loading and unloading cartridges 48 into the barrel 20 of the syringe. The main body frame 10 and the center pivot trigger 18 are fastened together with the trigger pivot sleeve screw 30a and the threaded sleeve 30b and pivot on each other in a scissors like fashion. The size of the trigger stop 19 molded into the main body frame 10, determines the length of the stroke of the center pivot trigger 18. The length of the stroke determines the size of the dosage to be administered by each particular syringe body. The main spring 44 is a compression spring and is mounted over the plunger rod 36 and is compressed within the enclosure of the operation window 41 and against the drag link 42 on its posterior end. The closure latch receiver 16 is molded to the top and front of the of the main body frame 10 and is rectangular in shape to match the shape of the closure latch 28. This allows the closure latch 28 to snap over and engage the closure latch receiver 16 when the cartridge 48 has been breech loaded into the syringe body and the barrel 20 and the main body frame 10 are rotated axially together to close the syringe body. The closure latch 28 and closure latch receiver 16 will hold the barrel 20 in that closed position. The crescent shaped plunger rod brake pivot 14, molded into the main body frame, holds the upper end of the plunger rod brake 38 in position. The plunger rod 36 is a flat rectangular rod, made of a hard material, threaded on each end for mounting the plunger rod handle 34 on the posterior end and the plunger pusher 46 on the anterior end. The plunger rod 36 is mounted through the aperture 38b in the plunger rod brake 38, through the main frame aperture 11a, through the aperture 42b in the drag link 42, through the main spring 44 and through the main frame aperture 11b. The drag link 42, also made of a hard material, is flattened and rectangular in shape. A rectangular hole or aperture 42b the same size and shape as the plunger rod 36 cross section is punched near the upper end of the drag link 42 with just enough tolerance to allow the plunger rod 36 to slide through the aperture 42b of the drag link 42. The plunger rod brake 38 is constructed similar to the drag link 42 only it is elongated and somewhat curved near the bottom end 38a to conform to the shape of the rear of the main body frame 10, where it is positioned. A properly sized aperture 38b is punched into the upper end of the plunger brake 38. The brake tension spring 40 is a compression spring, partially inset into a spring support hole 40a in the rear of the main body frame 10 and provides pressure on the plunger rod brake 38. The plunger rod handle 34 is a knob with a threaded hole, sized to screw onto the posterior end of the plunger rod 36 and is used for retracting the plunger rod 36.

The plunger pusher 46 is a disk with a threaded hole sized to screw onto the anterior end of the plunger rod 36 and is designed to push the plunger 56 forward in the cartridge 48 to expel the injectable product. All of the plastic parts of the syringe body, including the main body frame 10, the center pivot trigger 18, the barrel 20 and the plunger rod handle 34 will be colored the same as the color coded label 60 and the color coded posterior seal 58 on the cartridges sold with that syringe body. The dosage each different colored syringe body will administer will be specific to the product contained in the corresponding color coded cartridge 48. The manufacturer will calibrate the dosage level for the syringes at the factory by varying the size of the trigger stop 19, thereby restricting the stroke of the center pivot trigger 18. There will be no possibility of changing the dosage level or making any other adjustments to the syringe body or cartridge 48 on the farm.

Operation of Structures of FIGS. 1 to 8

The combination of the process of this invention and the operation of the syringe body utilizing the multidose disposable cartridge 48 begins at the pharmaceutical manufacturer where the injectable animal health product is packaged under sterile conditions in the disposable cartridge 48. The cartridge 48 is sealed on the anterior end by the twist on cap seal 52. The posterior end of the cartridge 48 is sealed by the plunger 56 and the color coded posterior seal 58 with pull ring 58*a* attached. The plunger 56 is held in the cartridge 48 by a snap in plunger retention ring 54. A color coded label 60 is glued to the cartridge 48. A corresponding color coded pistol grip syringe body is distributed in conjunction with the prefilled disposable cartridge 48. The manner of using the prefilled cartridge 48 in combination with the syringe body begins by removing the color coded posterior seal 58 from the posterior end of the prefilled cartridge 48 by pulling on the pull ring 58*a*. The next step is to open the syringe body to the loading position as is shown in FIG. 5. While grasping the syringe body in a normal pistol grip fashion with the right hand, the technician depresses the lower end of the plunger rod brake 38*a* with the right thumb and pulls the plunger rod handle 34 with the left hand until the plunger rod 36 is in the extreme rearward position as is shown in FIG. 6*c*. With the right thumb, the closure latch 28 is pushed slightly upward while applying downward pressure to the anterior top side of the barrel 20 with the left hand. The barrel 20 and main body frame 10 will rotate axially at the loading pivot 24 and loading pivot base 12, breaking open the syringe body into the open breech loading position as is shown in FIG. 5. The cartridge 48 is breech loaded into the barrel 20 of the syringe body just as shotgun shells are breech loaded into a shotgun. Care is taken to insure that the cartridge 48 is loaded with the dosage increment marks 62 facing upward so that they may be seen through the observation window 22. The barrel 20 is then rotated upward to its original closed position. As the barrel 20 approaches its final closed position the closure latch 28, which has some resiliency or spring action, rides up on the closure latch receiver 16 until the latch 28 snaps over the receiver rib 16 and secures the syringe in the closed position. The twist off cap seal 52 is removed from the twist lock needle adapter 50 and a new standard disposable needle is twist locked onto the twist lock needle adapter 50. The syringe is now ready for use.

To dispense the animal health product, the technician squeezes the center pivot trigger 18 which rotates axially on the trigger pivot sleeve screw 30*a* and threaded sleeve 30*b*, in a scissors like fashion in relation to the main body frame 10 as is shown in FIG. 6*b*. The striking surface 18*a* of the center pivot trigger 18 engages the bottom or lower end 42*a* of the drag link 42, moving the drag link 42 forward in the operation window 41. The pressure at the lower end of the drag link 42*a* creates an angle and a leveraged bind between the rectangular shaped aperture 42*b* in the drag link 42 and the rectangular shape of the plunger rod 36. The greater the distance between the striking edge of the trigger 18*a* and the lower end of the drag link 42*a*, the greater the leverage, power, and bind between the drag link 42 and the plunger rod 36. For optimum leverage and bind, a distance of twice the depth of the drag link aperture 42*b* is preferred, as is shown in FIG. 6*b*. Fully squeezing the center pivot trigger 18 drags the plunger rod 36 forward against the pressure from the main spring 44. The plunger rod 36 passes through and is guided by the front and rear main frame apertures 11*b* and 11*a*. As the plunger rod 36 advances forward, the plunger pusher 46 pushes the plunger 56 forward in the cartridge 48 forcing the animal health product from the cartridge 48, through the disposable needle into the flesh of the animal being treated, thereby dispensing one full dose of the product from the cartridge 48 into the animal. The needle protector collar 26 supplies reinforced support to avoid breakage of the twist lock needle adapter 50. The dosage level dispensed is controlled by the amount of free travel the center pivot trigger 18 is given which is predetermined by the size of the trigger stop 19 molded into the main body frame 10. When finger pressure is released from the center pivot trigger 18, the main spring 44 corrects the angle and slides the drag link 42 rearward along the plunger rod 36 returning the drag link 42 to its rest position, lying flush against the rear surface of the operation window 41 as is shown in FIG. 6*a*. The plunger rod 36 is held from moving rearward by the binding action of the plunger rod brake 38. The plunger rod brake 38 is held at the correct angle to bind the rearward motion on the plunger rod 36 by the brake tension spring 40. The plunger rod brake 38 is held in position at the top and pivoted at the plunger brake pivot 14. As the doses are dispensed, the technician may observe the position of the plunger 56 through the observation window 22. When the cartridge 48 is emptied the plunger rod 36 is retracted to its extreme rearward position by depressing the lower end 38*a* of the plunger rod brake 38 with a thumb and pulling back on the plunger rod handle 34 as is shown in FIG. 6*c*. The syringe body may then be opened, as was detailed earlier, into the loading or unloading position as is shown in FIG. 5 and the disposable cartridge 48 and disposable needle are removed and discarded.

Summary, Ramifications and Scope

Accordingly the reader will see that the process for handling vaccines and other injectable animal health products for livestock is dramatically improved through the use of this invention. The advantages listed below become apparent as the reader begins to visualize how the product is handled today and how that will change when the system utilizing the prefilled disposable cartridge and the described pistolgrip syringe body or dispensing mechanism is implemented.

Sanitary and sterile conditions are virtually guaranteed by the use of this invention. The product never makes any physical contact with any parts of the syringe body. The product is fully contained within the closed system of the prefilled disposable cartridge. A new clean and sterile disposable needle should be attached to each prefilled cartridge, therefore insuring that a new, sterile needle will be used at least each time a cartridge is emptied and a new, full cartridge is loaded. There is no transfer of the sterile product from its factory sterile container to a syringe that may or may not have been completely sterilized by the technician administering the injections.

No clean up of the syringes is necessary.

Rapid refilling is as quick and as easy as removing the spent cartridge and sliding a new one into the syringe.

There are no leaks and no waste of expensive product with this system.

Skips and short doses from mechanical wear are eliminated.

Made from a hard plastic material through the injection mold process, the cost of this syringe will be considerably lower as compared to the typical metal syringes which require extensive machining.

Mix ups in the work area will be greatly reduced because the labels of the cartridges will be color coded to match the syringes with which they are to be used. Cartridges will only fit into syringes that will administer the recommended dose for the product in the cartridges.

Although some example specifications are implied throughout the text of the above descriptions, these should not be construed as limiting the scope of the invention but as merely providing illustrations so that the reader may better visualize the embodiment of the invention. The size of both cartridges and syringes may be varied to fit specific consumer needs within the industry. This specific closed delivery system for injectable animal health products will work well for the treatment and vaccinations of all classes of livestock including beef cattle, dairy cattle, swine, sheep, goats, horses, poultry and other more exotic species.

Other embodiments of this invention may include:

1. The use of this system for other animal health products that require topical or inter-nasal application.

2. With a few structural changes but utilizing the same mechanical principles described in the above invention, the syringe may be modified to be used with the standard disposable syringes on the market today. As an example the technician would attach a disposable needle to a standard disposable syringe. The vaccine would be drawn into the disposable syringe from the standard container used today and the filled disposable syringe loaded into the modified pistol grip syringe body. The advantages to this system over the current system in use today are:

Vastly improved sterile conditions.
No cleaning of used syringes.
No leaking gaskets or plungers.
Less expensive syringe bodies.
A sterile method of handling modified live viruses that require mixing.
Rapid reloading of the syringe body.

3. The syringe body may be modified to employ a dosage adjustment mechanism for use with animal health products in which the recommended dosage may vary from animal to animal depending upon the size of the animal being treated.

Thus the scope of the invention should be determined by the appended claims and their legal equivalents, rather than by the examples given.

What is claimed is:

1. A device for handling and dispensing a biological product for livestock comprising:
  (a) a prefilled disposable cartridge containing sterile biological product; wherein said cartridge includes anterior and posterior ends and a plunger positioned in said posterior end; wherein said plunger is movable in said cartridge to dispense said biological product through said anterior end;
  (b) a pistol grip syringe body dispensing member including a main frame and further comprising:
    (i) a tubular barrel portion sized for receiving and supporting said cartridge; wherein said barrel portion is hinged to said main frame and is pivotal thereon between open and closed positions; wherein said cartridge is slidably inserted into or removed from said barrel portion when said barrel portion is in said open position;
    (ii) a trigger movably mounted on said frame and having an upper end; said trigger being movable between open and retracted positions; wherein said upper end moves in a forward direction when said trigger is moved to said retracted position;
    (iii) an elongated plunger rod having a forward end; wherein said plunger rod is axially aligned with said cartridge when positioned in said barrel portion;
    (iv) a link carried by said plunger rod and being engageable by said upper end of said trigger; wherein said link is adapted to engage and advance said plunger rod in said cartridge when said upper end of said trigger is moved in a forward direction;
    (v) brake means separate from the link and engagable with plunger rod and being adapted (1) to allow said plunger rod to be advanced by movement of said upper end of said trigger, and (2) to prevent rearward movement of said plunger rod;
  wherein movement of said trigger from said open position to said retracted position causes said plunger rod to advance said plunger in said cartridge.

2. A device in accordance with claim 1, further comprising color coding means, wherein said cartridge and said dispensing member each include the same color identification.

3. A device in accordance with claim 2, wherein said cartridge is sealed with a color-coded seal.

4. A device in accordance with claim 1, further comprising a needle detachably secured to said anterior end of said cartridge.

5. A device in accordance with claim 1, wherein said trigger is pivotally mounted on said dispensing member; and wherein movement of said trigger from said open to said retracted position causes said plunger rod to move against said plunger to thereby dispense a single dose of said biological product from said cartridge.

6. A device in accordance with claim 1, further comprising bias means for biasing said trigger toward its open position.

7. A closed delivery system for handling and dispensing a biological product for livestock comprising:
  (a) a prefilled disposable cartridge containing sterile biological product; wherein said cartridge includes anterior and posterior ends and a plunger positioned in said posterior end; wherein said plunger is movable in said cartridge to dispense said biological product through said anterior end;
  (b) a pistol grip syringe body dispensing member including a main frame and further comprising:
    (i) a tubular barrel portion sized for receiving and supporting said cartridge; wherein said barrel portion is hinged to said main frame and is pivotal thereon between open and closed positions; wherein said cartridge is slidably inserted into or removed from said barrel portion when said barrel portion is in said open position;
    (ii) a trigger movably mounted on said frame and having an upper end;
    (iii) a link including an aperture therethrough;
    (iv) an elongated plunger rod having a forward end; wherein said plunger rod extends through said aperture in said link and is axially aligned with said cartridge when positioned in said barrel portion;
    (v) bias means for biasing said link toward said upper end of said trigger;
  wherein said aperture in said link is sized such that movement of said upper end of said trigger toward said cartridge causes said upper end to engage said link and cause it to tilt relative to said plunger rod so as to frictionally engage said plunger rod and thereby move said plunger rod against said plunger in said cartridge; and wherein said bias means is adapted to move said link rearwardly with respect to said plunger rod when said trigger is released.

8. A system in accordance with claim 7, further comprising color coding means wherein said cartridge and said dispensing member each include the same color identification.

9. A system in accordance with claim 7, wherein said trigger is pivotally mounted on said dispensing member and is movable between open and retracted positions; wherein movement of said trigger from said open to said retracted position causes said plunger rod to move against said plunger to thereby dispense a single dose of said biological product from said cartridge.

10. A closed delivery system for handling and dispensing a biological product for animals comprising:

(a) a prefilled disposable cartridge containing sterile biological product; wherein said cartridge includes anterior and posterior ends and a plunger positioned in said posterior end; wherein said plunger is movable in said cartridge to dispense said biological product through said anterior end;

(b) a pistol grip syringe body dispensing member including a main frame and further comprising:

(i) a tubular barrel portion sized for receiving and supporting said cartridge; wherein said barrel portion is carried by said main frame;

(ii) a trigger movably mounted having an upper end;

(iii) a link including an aperture therethrough;

(iv) an elongated plunger rod having a forward end; wherein said plunger rod extends through said aperture in said link and is axially aligned with said cartridge;

(v) bias means for biasing said link toward said upper end of said trigger:

(vi) brake means separate from the link and engagable with plunger rod and being adapted (1) to allow said plunger rod to be advanced by movement of said upper end of said trigger, and (2) to prevent rearward movement of said plunger rod;

wherein said aperture in said link is said such that movement of said upper end of said trigger toward said cartridge causes said upper end to engage said link and cause it to tilt relative to said plunger rod so as to frictionally engage said plunger rod and thereby move said plunger rod against said plunger in said cartridge; and wherein said bias means is adapted to move said link rearwardly with respect to said plunger rod when said trigger is released.

11. A system in accordance with claim 10, further comprising color coding means wherein said cartridge and said dispensing member each include the same color identification.

* * * * *